Feb. 16, 1954 H. C. SWIM Plant Pat. 1,255
ROSE PLANT
Filed Feb. 9, 1953
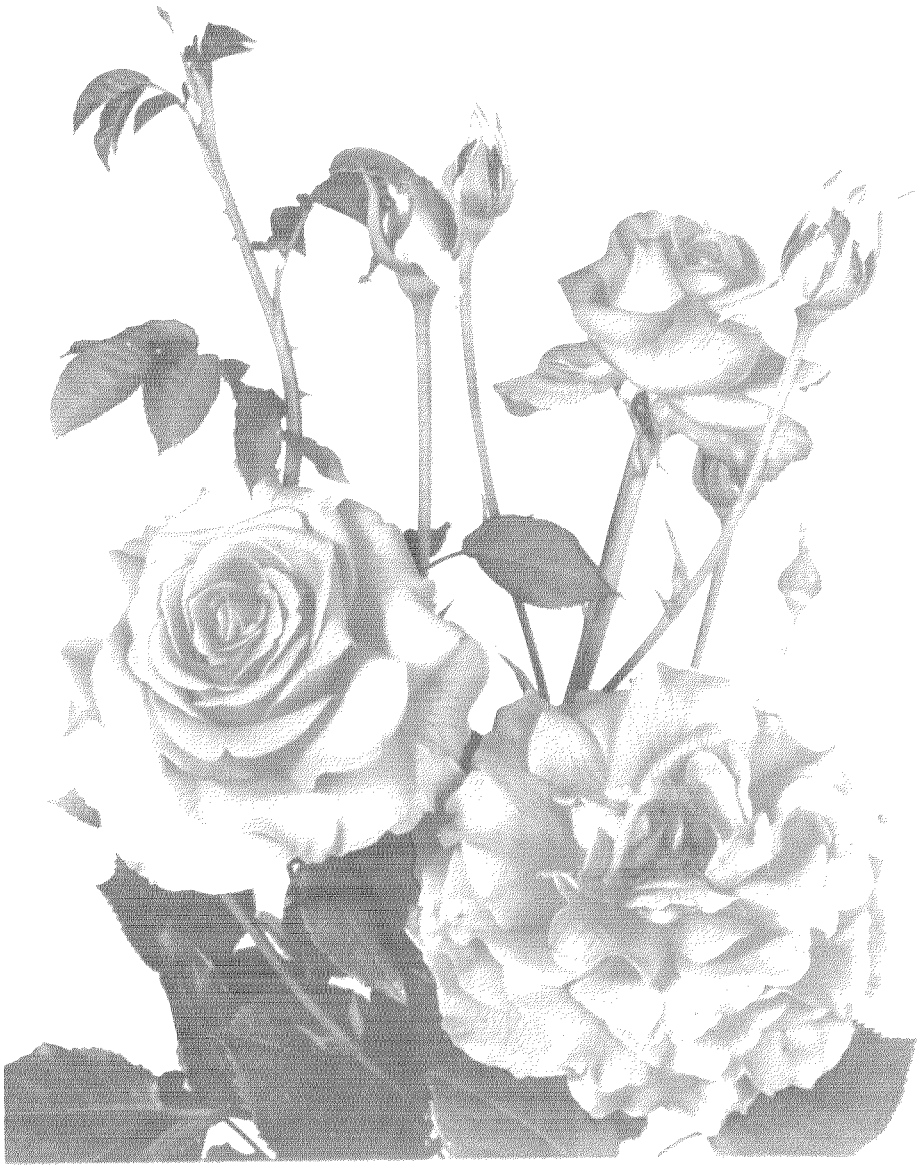
Inventor
H. C. Swim
By: Robert Cobb
Attorneys.

Patented Feb. 16, 1954

Plant Pat. 1,255

UNITED STATES PATENT OFFICE 1,255

ROSE PLANT

Herbert C. Swim, Ontario, Calif., assignor, by mesne assignments, to Breedlove Nurseries, a partnership Application February 9, 1953, Serial No. 336,029

1 Claim. (Cl. 47—61)

The present invention relates to a new and distinct variety of rose plant of the hybrid tea class, which was produced by me as the result of crossing the variety "Crimson Glory" (Plant Patent No. 105) with the variety "Girona" (unpatented).

The primary objective in making this cross was to produce a new variety of rose plant which combines the best characteristics of the two parent varieties. This objective was fully attained, as evidenced by the following unique combination of outstanding characteristics which distinguish my new variety from its parents, as well as from all other varieties of its class:

(1) The vigorous habit of growth of the plant, as inherited from the pollen parent "Girona";

(2) The much-branched habit of the plant as inherited from its seed parent "Crimson Glory," together with an upright habit of growth inherited from the pollen parent;

(3) The presence of very few prickles on the flowering stems, which is typical of "Girona";

(4) The longer-than-average flowering stem and peduncle, typical of "Girona";

(5) The leathery and semi-glossy foliage that is typical of "Girona," with an abundance of foliage which is typical of "Crimson Glory"; and (6) The distinctive color and very double petalage of the flowers of the new variety, as hereinafter more specifically described.

In comparison with its seed parent "Crimson Glory," the blooms of my new variety are pink in general color tonality, whereas the blooms of "Crimson Glory" are dark red or more popularly described as deep velvety crimson—the upright habit of growth of the new variety is quite distinct from the bushy and spreading growth of this parent; the flowers of the new variety have many more petals than those of its parent, the former usually averaging from 50 to 60 petals, and the latter being semi-double and averaging not more than 18 to 25 petals; there are fewer prickles on the flowering stems of my new variety than are found on the flowering stems of the parent; and the foliage of the new variety is larger in size and of heavier substance than the foliage of "Crimson Glory."

As compared with its pollen parent "Girona," the pink blooms of my new variety are quite different from those of this parent, the latter being multi-colored in various soft shades of pink, yellow and carmine; the foliage of my new variety is more abundant and covers the plant more completely than does the foliage of "Girona"; and the increased petalage of the blooms of the new variety sharply contrasts with the fewer petals in the blooms of "Girona" which usually average from 20 to 30 petals.

Asexual reproduction of my new variety by budding at Ontario, California, shows that the foregoing characteristics and distinctions come true to form and are established and transmitted through succeeding propagations.

The accompanying illustration shows typical specimens of the blooms, stems and foliage of my new variety in different stages of development.

The following is a detailed description of my new variety, with color terminology in accordance with Robert F. Wilson's Horticultural Colour Chart (hereinafter designated as "Wilson") and with Ridgway's Color Standards and Nomenclature (hereinafter designated as "Ridgway"), except where general color terms of ordinary dictionary significance are obvious:

Type: Outdoor; seedling; for cut flowers and garden decoration.

Class: Hybrid tea.

Breeding: Seedling.

*Seed parent.*—"Crimson Glory."

*Pollen parent.*—"Girona."

Propagation: Holds its distinguishing characteristics through succeeding propagations by budding.

*Flower*

Locality where grown and observed: Ontario, California.

Flowers borne: Sometimes singly, but sometimes 3 to 5 or more to basal stem; on normal strength, medium to long stems.

Quantity of bloom: Abundant, outdoors.

Continuity: Nearly continuous during growing season.

Fragrance: Moderate to penetrating; spicy.

Bud:

*Peduncle.*—Average length to long; average caliper; erect; usually smooth; some gland-tipped cilia; numerous hairs. Color —near Lettuce Green, Plate V (Ridgway).

*Before calyx breaks.*—Size—medium. Form —medium length; ovoid; with glabrous foliaceous appendages on the surface of the bud; sometimes with stout, much-cut, bristle-like foliaceous parts extending beyond the tip of the bud equal to from ¼ to ½ of its length.

*As calyx breaks.*—Color—near Rose Opal, Plate 022/1, page 110 (Wilson), marked with near Indian Lake, Plate 826, page 170 (Wilson).

*Sepals.*—Inner surface with fine, woolly tomentum. Margins: alternate sepals with woolly tomentum and a few stipitate glands; others lined with stipitate glands and some hairs.

*As first petal opens.*—Size—average. Form—medium length; ovoid to broadly ovoid. Color: outside—between Tyrian Rose, Plate 24/2, page 24 (Wilson) and Tyrian Rose, Plate 24/3, page 24 (Wilson); small area at base of petal near attachment near Aureolin, Plate 3/2, page 3 (Wilson); inside—between Rose Madder, Plate 23/1, page 23 (Wilson) and Tyrian Rose, Plate 24/2, page 24 (Wilson); small area at base of petal near attachment near Aureolin, Plate 3/1, page 3 (Wilson).

*Opening.*—Opens up well; is not retarded from opening by cold, hot, wet or dry weather.

Bloom:

*Size, when fully open.*—Average to large; 3¾ inches to 5 inches.

*Petalage.*—Very double; from 50 to 60 petals, plus 20 to 25 petaloids; arranged regularly.

*Form.*—High-centered at first; becoming flat to open; petals being at first somewhat flat-cupped, with lateral margins reflexed over ½ to ¾ of upper portion of petal, and apex sometimes somewhat reflexed; becoming flat later at maturity, with apex reflexed somewhat and lateral margins reflexed for about ¾ of upper portion of petal.

Petals:

*Texture.*—Medium thickness; leathery; with inside velvety and outside satiny.

*Shape.*—Outside—broadly obovate, with apex flat and rarely with notches. Intermediate—broadly obovate, with apex rounded to flat and with rarely any notches. Inside—obovate; irregular, with apex rounded and sometimes with 1 or 2 notches.

This description of a newly opened flower was made from a rose grown outdoors in the month of May, at Ontario, California:

*Color.*—Outside petal: outside surface—near Rose Bengal, Plate 25/3, page 25 (Wilson); small area at base of petal near attachment near Aureolin, Plate 3/2, page 3 (Wilson); inside surface—between Tyrian Rose, Plate 24/2, page 24 (Wilson) and Rose Bengal, Plate 25/2, page 25 (Wilson); small area at base of petal near attachment near Aureolin, Plate 3/1, page 3 (Wilson). Intermediate petal: outside surface—near Rose Bengal, Plate 25/3, page 25 (Wilson); small area at base of petal near attachment near Aureolin, Plate 3/1, page 3 (Wilson); inside surface—between Tyrian Rose, Plate 24/2, page 24 (Wilson) and Rose Bengal, Plate 25/2, page 25 (Wilson); small area at base of petal near attachment near Aureolin, Plate 3/1, page 3 (Wilson). Inner petal: outside surface—between Crimson, Plate 22/2, page 22 (Wilson) and Rose Madder, Plate 23/1, page 23 (Wilson); small area at base near attachment near Aureolin, Plate 3/1, page 3 (Wilson); inside surface—between Crimson, Plate 22/1, page 22 (Wilson) and Rose Madder, Plate 23/1, page 23 (Wilson); small area at base near attachment near Aureolin, Plate 3/1, page 3 (Wilson).

This description was made from a rose that was open for 3 days outdoors in the month of May, at Ontario, California:

*Color.*—Outside petal: outside surface—between Tyrian Rose, Plate 24/3, page 24 (Wilson) and Rose Bengal, Plate 25/3, page 25 (Wilson); small area at base of petal near Aureolin, Plate 3/1, page 3 (Wilson); inside surface—between Rose Bengal, Plate 25/2, page 25 (Wilson) and Rose Bengal, Plate 25/3, page 25 (Wilson); small area at base of petal near Aureolin, Plate 3/1, page 3 (Wilson). Inside petal: outside surface—between Rose Madder, Plate 23/2, page 23 (Wilson) and Rose Madder, Plate 23/3, page 23 (Wilson); small area at base of petal near attachment near Aureolin, Plate 3/1, page 3 (Wilson); inside surface—near Rose Madder, Plate 23/1, page 23 (Wilson); small area at base of petal near Aureolin, Plate 3/1, page 3 (Wilson).

*General color tonality.*—Newly opened flower—between Rose Madder, Plate 23/1, page 23 (Wilson) and Tyrian Rose, Plate 24/2, page 24 (Wilson). 3-days open—between Tyrian Rose, Plate 24/2, page 24 (Wilson) and Rose Bengal, Plate 25/2, page 25 (Wilson); small area at base near attachment near Aureolin, Plate 3/1, page 3 (Wilson).

*Behavior.*—Drop off cleanly; not particularly affected by cold, hot, wet or dry weather.

*Flower longevity.*—On bush in garden—3 to 4 days in May. Cut roses grown outdoors and kept at living-room temperatures—3 days in May.

*Reproductive organs*

Stamens: Average number to many; arranged regularly about pistils; a few mixed with petaloids.

Filaments: Medium length; 8 to 12 mm. long; most with anthers. Color—between Aureolin, Plate 3/2, page 3 (Wilson) and Lemon Yellow, Plate 4/2, page 4 (Wilson).

Anthers: Medium size to large; all open approximately at once. Color—upper side—margin near Buttercup Yellow, Plate 5/2, page 5 (Wilson; remainder near Aureolin, Plate 3/2, page 3 (Wilson). Under side—margin Buttercup Yellow, Plate 5/2, page 5 (Wilson); remainder near Aureolin, Plate 3/2, page 3 (Wilson).

Pollen: Moderate to abundant. Color—between Lemon Yellow, Plate 4, page 4 (Wilson) and Buttercup Yellow, Plate 5/3, page 5 (Wilson).

Pistils: Many; approximately 130 in number.

Styles: Moderately even; average length; average caliper; bunched; 7 to 10 mm. long. Color—near Sap Green, Plate 62/3, page 62 (Wilson); near Carmine, Plate 21/1, page 21 (Wilson) towards stigma.

Stigma: Color—near Empire Yellow, Plate 603/3, page 66 (Wilson).

Ovaries: Most enclosed in, but some protruding from, calyx.

Hips: Average length; globular; with inconspicuous neck; smooth; walls thick and fleshy. Color (half mature)—between Lettuce Green, Plate V (Ridgway) and Parrot Green, Plate VI (Ridgway).

Sepals: Permanent; medium length; recurved. Color: inside—near Lettuce Green, Plate V (Ridgway), masked by white tomentum; outside—between Cosse Green, Plate V (Ridgway) and Lettuce Green, Plate V (Ridgway).

Seeds: Few to average number; medium size; from 6 to 10 in number.

*Plant*

Foliage:

*Leaves.*—Compound of usually 5 to 7 leaflets; normal abundance; medium size to large; leathery; semi-glossy.

*Leaflets.*—Shape—ovoid, with acute apex, and round base. Margin—simply serrate.

*Color.*—Mature: upper surface—near Dark Dull Yellow-Green, Plate XXXII (Ridgway); under surface—near Parrot Green, Plate VI (Ridgway). Young: upper surface—near Cress Green, Plate XXXI (Ridgway), shaded with near Dark Corinthian Purple, Plate XXXVIII (Ridgway); under surface—near Neutral Red, Plate XXXVIII (Ridgway).

*Rachis (the supporting stem of the compound leaf).*—Average size. Upper side—grooved, with some stipitate glands on edges. Under side—sparsely prickly.

*Stipules.*—Medium length; medium width to wide; with medium length points turning out at an angle of more than 45°.

*Disease.*—Average resistance to mildew, as compared with other varieties grown under comparable cultural conditions at Ontario, California.

Growth:

*Habit.*—Upright; much-branched.

*Growth.*—Vigorous.

*Canes.*—Heavy.

*Main stems.*—Color—near Oil Green, Plate V (Ridgway). Large prickles—several; medium length; hooked very slightly downward; with medium length, narrow base. Color—near Drab Gray, Plate XLVI (Ridgway). Small prickles—none. Hairs—none.

*Branches.*—Color—near Parrot Green, Plate VI (Ridgway). Large prickles—several; medium length; hooked very slightly downward; with medium length, narrow base. Color—near Cinnamon-Brown, Plate XV (Ridgway). Small prickles—Few. Color—between Russet, Plate XV (Ridgway) and Cinnamon-Brown, Plate XV (Ridgway). Hairs—none.

*New shoots.*—Color—between Calliste Green, Plate VI (Ridgway) and Parrot Green, Plate VI (Ridgway), heavily shaded with between Perilla Purple, Plate XXXVII (Ridgway) and Dark Perilla Purple, Plate XXXVII (Ridgway). Large prickles—several; medium length; hooked only slightly downward; with medium length, narrow base. Color—near Corinthian Purple, Plate XXXVIII (Ridgway). Small prickles—few. Color—between Vernonia Purple, Plate XXXVIII (Ridgway) and Corinthian Purple, Plate XXXVIII (Ridgway). Hairs—none.

I claim:

A new and distinct variety of rose plant of the hybrid tea class, substantially as herein shown and described, characterized particularly as to novelty by its unique combination of vigorous, much-branched and upright habits of growth, its relatively few prickles on its flowering stems, the longer-than-average flowering stems and peduncles, the abundance of its leathery and semi-glossy foliage, and the distinctive color and very double petalage of its blooms.

HERBERT C. SWIM.

No reference cited.